(12) United States Patent
Bleth et al.

(10) Patent No.: US 10,595,538 B1
(45) Date of Patent: Mar. 24, 2020

(54) SYSTEM AND METHOD OF AUTOMATED EXTRACTION

(71) Applicant: Harrison Poultry, Inc., Bethlehem, GA (US)

(72) Inventors: David Bleth, Bethlehem, GA (US); Jens Eysteinsson, Monroe, GA (US)

(73) Assignee: Harrison Poultry, Inc., Bethlehem, GA (US)

( * ) Notice: Subject to any disclaimer, the term of this patent is extended or adjusted under 35 U.S.C. 154(b) by 0 days.

(21) Appl. No.: 16/541,805

(22) Filed: Aug. 15, 2019

Related U.S. Application Data

(60) Provisional application No. 62/860,400, filed on Jun. 12, 2019.

(51) Int. Cl.
*A22B 5/00* (2006.01)

(52) U.S. Cl.
CPC .................. *A22B 5/0005* (2013.01)

(58) Field of Classification Search
CPC .............................. A22B 5/00; A22B 5/0005
USPC .......................... 452/106–109, 120
See application file for complete search history.

(56) References Cited

U.S. PATENT DOCUMENTS

| | | | |
|---|---|---|---|
| 5,041,053 A * | 8/1991 | Ellis .................. | A22C 21/06 452/106 |
| 5,120,266 A * | 6/1992 | Aubert .................. | A22B 5/0094 452/106 |
| 8,992,290 B2 * | 3/2015 | Taniguchi ............ | A22C 17/004 452/135 |

FOREIGN PATENT DOCUMENTS

| | | |
|---|---|---|
| CN | 1850846 B | 4/2010 |
| CN | 102060902 A | 5/2011 |

* cited by examiner

*Primary Examiner* — Richard T Price, Jr.
(74) *Attorney, Agent, or Firm* — Maier & Maier, PLLC

(57) ABSTRACT

The present invention is an improved system and method of automatic extraction. The system of automatic extraction includes a processing line, a pan, a bile source, an imaging system, a targeting system, and an extraction tool. The processing line moves one or more pans with one or more bile sources on each pan. An imaging system and targeting system coordinate to target bile sources with an extraction tool using a coordinate system. A method of automatic extraction includes locating a bile source on a coordinate system, targeting the bile source, puncturing the bile source with an extraction tool, extracting bile from a source, and storing the extracted bile.

20 Claims, 9 Drawing Sheets
(4 of 9 Drawing Sheet(s) Filed in Color)

SYSTEM AND METHOD OF AUTOMATED EXTRACTION

CROSS-REFERENCE TO RELATED APPLICATIONS

This application claims benefit of U.S. Provisional Patent Application No. 62/860,400, filed Jun. 12, 2019, the entire contents of which are incorporated herein by reference.

BACKGROUND

Chenodeoxycholic acid (CDCA) is one of two primary bile acids in human beings and facilitates lipid digestion. The pharmaceutical industry can use CDCA for therapeutic purposes including preventative care and treatments for gallstone disorders, cerebrotendineous xanthomatosis, liver disease, heart disease, and potentially even Hepatitis C. Another use of CDCA is the production of Ursodeoxycholic acid (UDCA), a secondary bile acid. UDCA has significant pharmaceutical importance for its uses relating to obesity, primary biliary cirrhosis, cystic fibrosis, and a number of other conditions.

CDCA can be synthesized, as shown in CN102060902A ("Chenodeoxycholic acid synthesis method"). Synthesis requires extraction and/or production of costly ingredients, along with intensive labor and time.

CDCA is naturally occurring not just in human beings, but in some animals including chickens and geese as well, providing a readily available source for CDCA. Some of these animals are used in the poultry industry, such as chickens, turkeys, ducks, and geese. Extraction of bile from chickens can yield 1.8-3.0 mL of bile per gall bladder. Individual poultry plants process upwards of 165,000 birds each shift, which could provide 200 or more liters of CDCA each shift. This represents a significant potential source of CDCA and could provide more CDCA for the pharmaceutical industry to treat more patients who need it.

Unfortunately, the extraction processes for obtaining the bile from these gall bladders is time consuming, labor intensive, and expensive. One exemplary method of the current processes is described in CN1850846B ("Production method for extracting chenodeoxycholic acid using chicken gall"). This process includes cutting and freezing chicken into thin slices, cooking the slices, and various other labor-intensive steps.

These highly labor intensive and inefficient processes are not currently compatible with the poultry industry. Poultry processing is highly automated and fast moving, using evisceration lines to prepare the birds. Evisceration lines at poultry processing plants can process 140 or more birds each minute as part of a finely tuned system. The inefficiency of these current CDCA processes makes integration into the evisceration lines infeasible as they would burden the preparation process significantly and vastly diminish the production volume.

SUMMARY

Accordingly, it is an object of the present invention to provide an improved system and method of automatic extraction. According to at least one exemplary embodiment, a system of automatic extraction may include a processing line, a pan, a bile source, an imaging system, a targeting system, and an extraction tool. A processing line may move one or more pans with one or more bile sources on each pan. An imaging system and targeting system may coordinate to target bile sources with an extraction tool using a coordinate system. According to at least one exemplary embodiment, a method of automatic extraction may include locating a bile source on a coordinate system, targeting the bile source, puncturing the bile source with an extraction tool, extracting bile from a source, and storing the extracted bile.

BRIEF DESCRIPTION OF THE FIGURES

The patent or application file contains at least one drawing executed in color. Copies of this patent or patent application publication with color drawing(s) will be provided by the Office upon request and payment of the necessary fee.

Advantages of embodiments of the present invention will be apparent from the following detailed description of the exemplary embodiments thereof, which description should be considered in conjunction with the accompanying drawings in which like numerals indicate like elements, in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequences of actions described herein can be considered to be embodied entirely within any form of non-transitory computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

According to an exemplary embodiment, and referring generally to the Figures, various exemplary implementations of a system and method for automated extraction may be disclosed.

Figure 1:
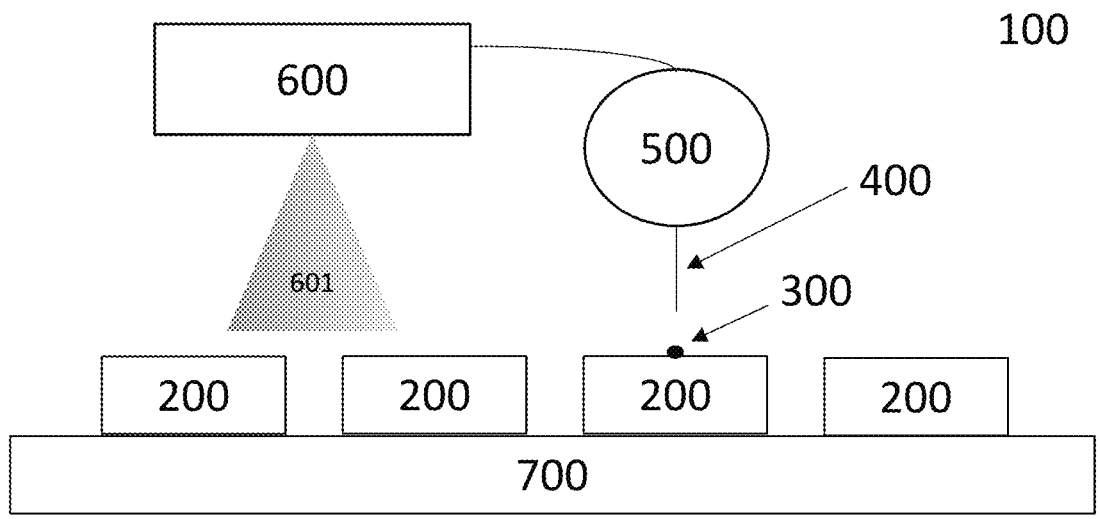
FIG. 1 is an exemplary embodiment of a system of automated extraction.

Turning now to exemplary FIG. 1, FIG. 1 displays an exemplary embodiment of a system of automated extraction 100. A system of automated extraction 100 may include a processing line 700, one or more pans 200, a bile source 300, an extraction tool 400, a targeting system 500, and an imaging system 600. The system of automated extraction 100 may include a processing line 700 which moves continuously. The processing line 700 may carry one or more pans 200 and move the pans 200 in a continuous line. The processing line 700 is configured to move at an adjustable speed. The one or more pans 200 may be integral with the processing line 700 or separate from the processing line 700. For example, in some exemplary embodiments the processing line 700 comprises a conveyor formed from interconnected pans 200, and in some exemplary embodiments the processing line 700 is in the form of a conveyor surface configured to receive the one or more pans 200. The pans 200 may be, for example, Meyn Maestro pans. Each pan 200 may be sized to carry a bile source 300. The bile source 300 may be a gall bladder. The bile source 300 may come from a chicken, turkey, a goose, a duck, or any other animal. The bile source 300 may be inside of general viscera from an animal. The viscera may be styled to make the bile source 300 more visible or detectable. Styling may include flipping, rotating, opening or otherwise arranging on the pan 200.

Figure 2:
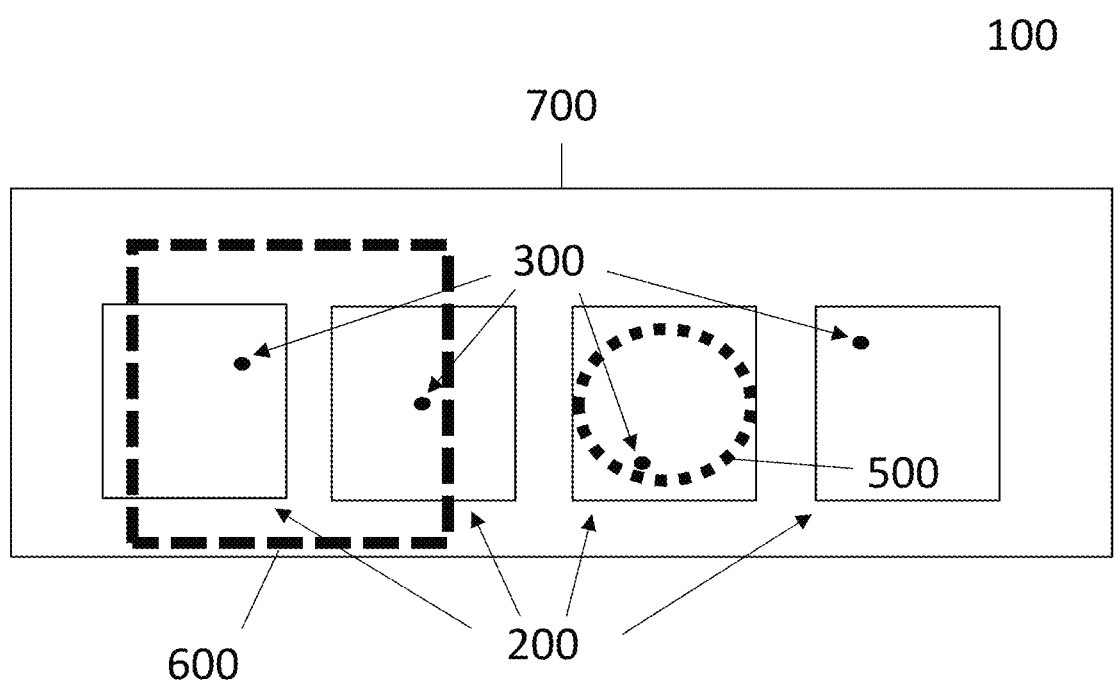
FIG. 2 is an exemplary embodiment of a system of automated extraction.

Turning now to exemplary FIG. 2, FIG. 2 displays an exemplary embodiment of a system of automated extraction 100, as viewed from above the processing line 700. The system of automated extraction 100 includes the processing line 700, one or more pans 200, the bile source 300, the extraction tool 400 (not shown in FIG. 2), the targeting system 500, and the imaging system 600. The processing line 700 may carry pans 200 with bile sources 300 past the imaging system 600 and the targeting system 500. In some exemplary embodiments, as illustrated in FIG. 2, the imaging system 600 and the targeting system 500 are positioned above the process line 700. In other exemplary embodiments the imaging system 600 and/or the targeting system 500 may be located next to the process line 700.

The imaging system 600 may produce a field of view 601 that includes a processing line 700. As shown in FIG. 1, the field of view 601 may extend from above the processing line 700. The imaging system 600 may produce videos, photos, x-rays, sonograms, or any other form of imaging. The imaging system 600 may include one or more cameras or receivers. The imaging system 600 may capture continuously, for example, as the processing line 700 moves. The imaging system 600 may instead be equipped with a timer and timed to capture images according to a predetermined cycle time, or the imaging system 600 may be equipped with another timing mechanism so as to synchronize the capturing of images with the movement of the processing line 700, the pans 200, and/or the bile source 300. The imaging system 600 may be tuned to identify specific objects in its field of view 601, such as the bile source 300 or a more specific target such as a gall bladder surrounded by viscera. The imaging system 600 may be connected to the targeting system 500.

The targeting system 500 may have an extraction tool 400 attached to it. The targeting system 500 may receive information from the imaging system 600, such as the location of a target, such as a bile source 300, or specifically a gall bladder surrounded by viscera. The targeting system 500 may use the location information from the imaging system 600 to align the extraction tool 400 with respect to a given target, such as bile source 300, as shown in FIG. 1. The targeting system 500 may be able to align the extraction tool 400 in one or more horizontal directions. The targeting system 500 may be able to align the extraction tool 400 vertically.

Figure 3:
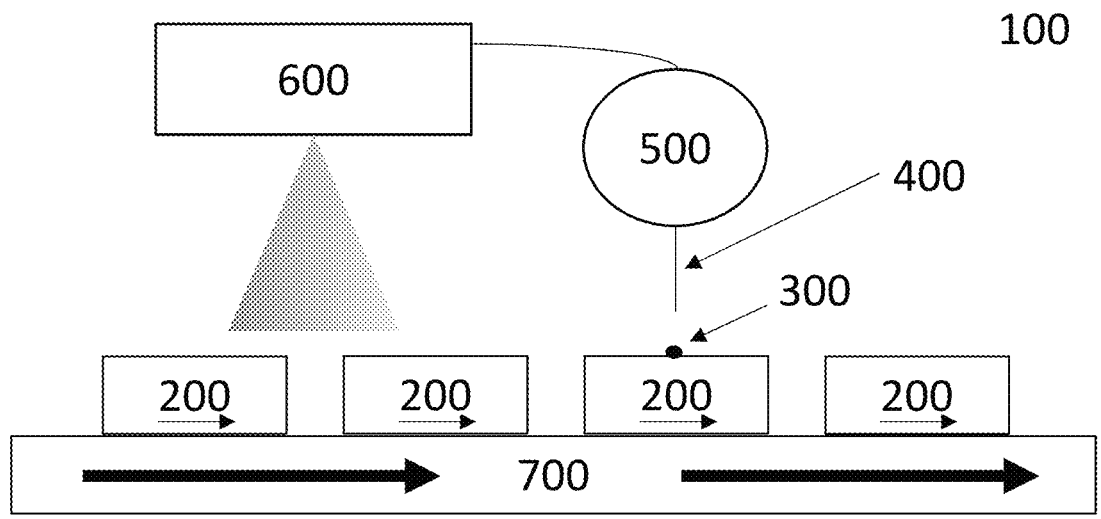
FIG. 3 is an exemplary embodiment of a system of automated extraction.
Figure 4:
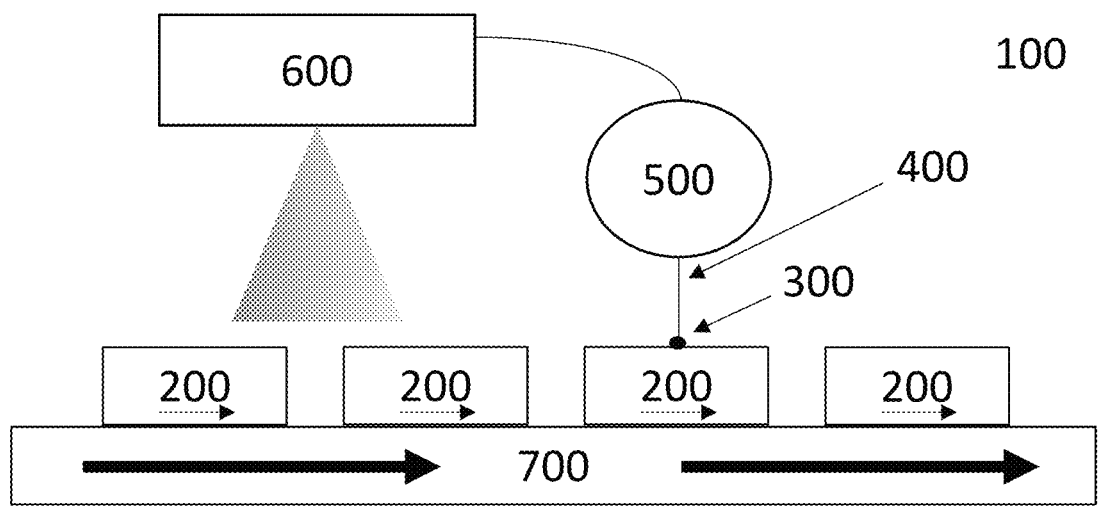
FIG. 4 is an exemplary embodiment of a method of automated extraction.

Turning now to exemplary FIGS. 3 and 4, FIGS. 3 and 4 display an exemplary embodiment of a system of automated extraction. The system of automated extraction 100 may include a processing line 700, one or more pans 200, a bile source 300 being carried by one or more pans 200, a targeting system 500 including an extraction tool 400, and an imaging system 600. The processing line 700 may carry pans 200 with bile sources 300 to and from an extraction tool 400. As illustrated in the embodiment of FIGS. 3 and 4, the targeting system 500, the extraction tool 400 and the imaging system 600 are positioned above the processing line 700 with pans 200. The processing line 700 with pans 200 passes under the imaging system 600 and then passes under the targeting system 500 with extractions tool 400. The processing line 700 is equipped with a variable speed drive, which may move the processing line 700 at speeds from 100 to 200 bile sources per minute to provide sufficient time for the extraction tool 400 to puncture the bile sources 300 and extract the bile by suction. The extraction tool 400 may be a needle, a tube, or another tool otherwise capable of puncture and suction. The extraction tool 400 may also include more than one or multiple needles or tubes to increase the extraction efficiency. In some exemplary embodiments the extraction tool is configured to provide a rate of extraction from 1.5 mL to 3.0 mL over a 4 to 5 second period. The targeting system 500 may align the extraction tool 400 in relation to a bile source 300 carried by a pan 200 on the processing line 700 according to information received from an imaging system 600. The targeting system 500 may then move the extraction tool 400 towards the bile source 300 for extraction of the bile. The extraction tool 400 may instead extend towards the bile source 300 or otherwise approach the bile source 300. The extraction tool 400 may then be capable of moving away from bile source 300. Frequency of extraction may be variable to account for variability of the processing line 700 speed. For example, in some exemplary embodiments, the number of bile sources 300 subjected to extraction is from 100 to 200 bile sources 300 per minute (pending line speed of evisceration lines). The movement of the extraction tool 400 may be synchronized with pans 200 on the processing line 700. The synchronization may be achieved by running the extraction tool 400 and the processing line 700 on a single power shaft. The extraction tool 400 may be connected to a storage tank. The storage tank may hold and preserve bile.

Figure 5:
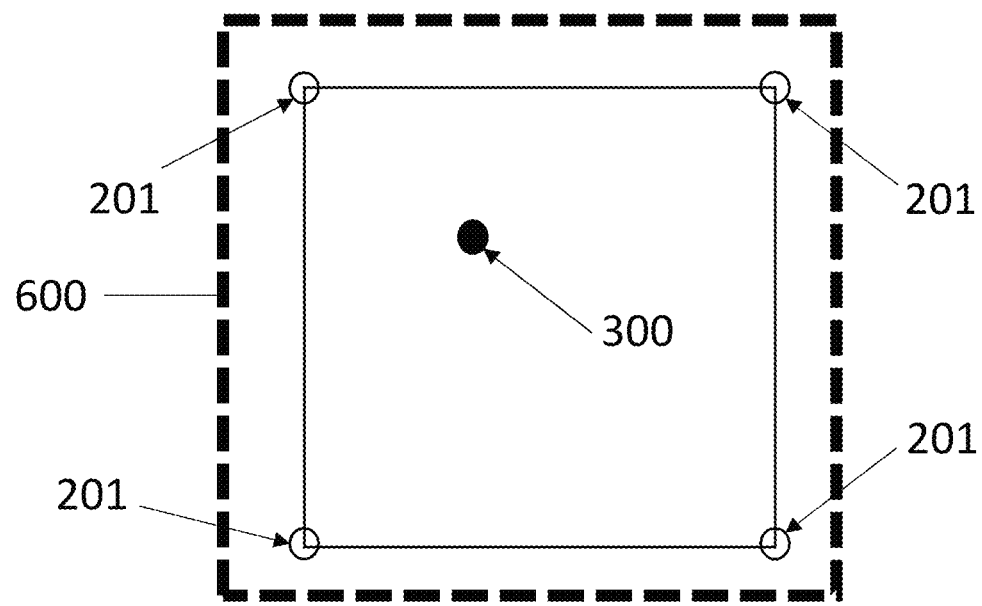
FIG. 5 is an exemplary embodiment of a method of automated extraction.
Figure 6:
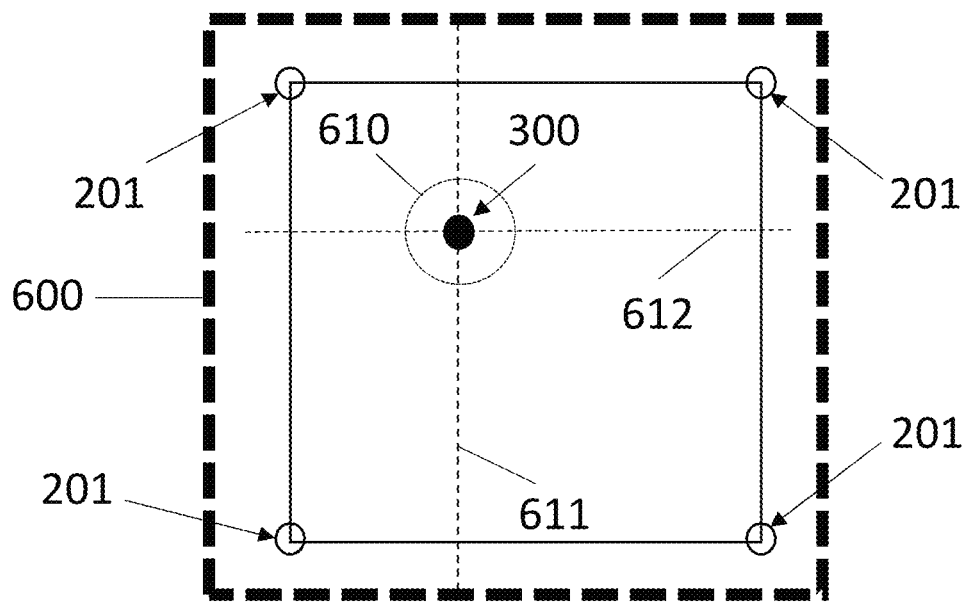
FIG. 6 is an exemplary embodiment of a method of automated extraction.
Figure 9:
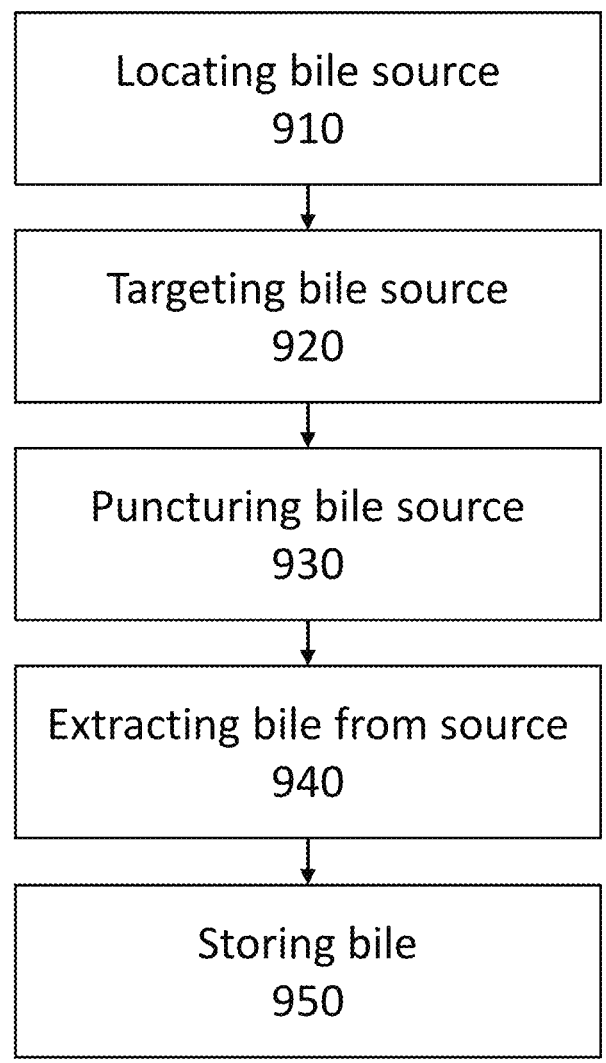
FIG. 9 is an exemplary embodiment of a method of automated extraction.

Turning now to exemplary FIGS. 5 and 6, FIGS. 5 and 6 display an exemplary embodiment of a method of automated extraction concerning the imaging system 600 and pan 200 carrying a bile source 300. A method of automated extraction 900, as illustrated in FIG. 9, may include locating a bile source 910, targeting a bile source 920, puncturing a bile source 930, extracting bile from a source 940, and storing bile 950. Locating a bile source 910 may be achieved using an imaging system 600 as displayed in FIGS. 5 and 6. The imaging system 600 may locate the bile source 300 on the pan 200. The bile source 300 may be identified by its color, its size, its shape, its composition, or any other distinguishing traits from its surroundings. The pan 200 contents may have been styled to make the bile source 300 more visible or detectable. Styling may include flipping, rotating, opening or otherwise arranging on the pan 200. The imaging system may use the corners 201 of the pan 200. The corners 201 may be used to define a coordinate system. The coordinate system may be used to define the location of the bile source 300. The bile source 300 may be located using a circle 610, which surrounds the bile source 300. The bile source 300 may be located using y-coordinate line 611 and x-coordinate line 612. The imaging system 600 may then send the location of the bile source 300 to the targeting system 500.

Figure 7:
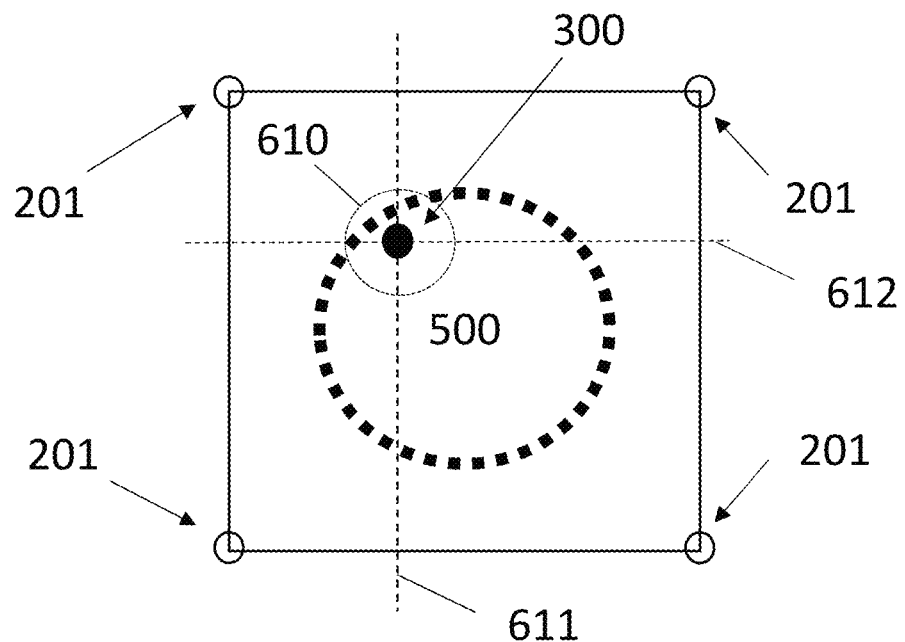
FIG. 7 is an exemplary embodiment of a method of automated extraction.
Figure 8:
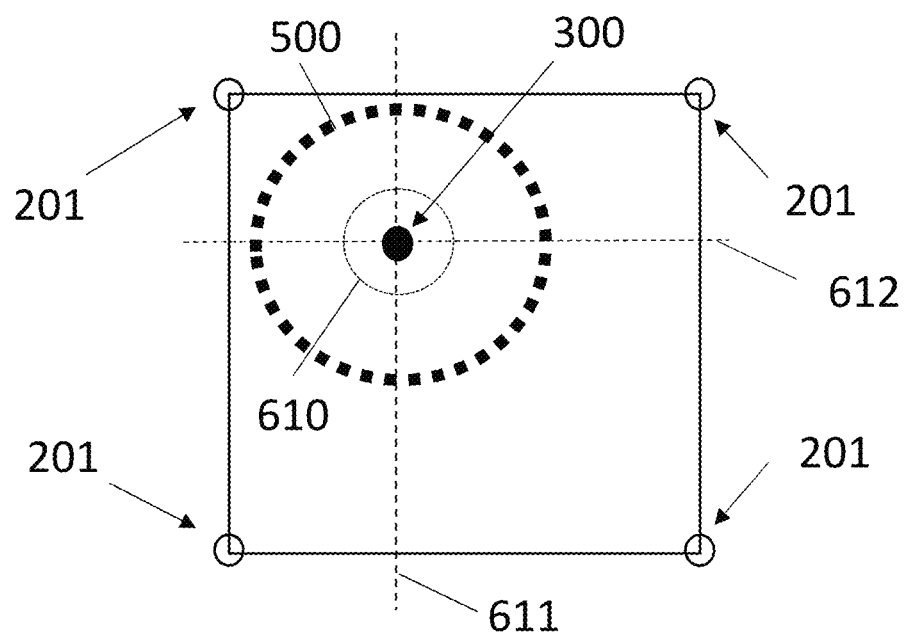
FIG. 8 is an exemplary embodiment of a method of automated extraction.

Turning now to exemplary FIGS. 7 and 8, FIGS. 7 and 8 display an exemplary embodiment of a method of automated extraction concerning the targeting system 500 and pan 200 carrying a bile source 300. As illustrated in FIG. 9, a method of automated extraction 900 may include locating a bile source 910, targeting a bile source 920, puncturing a bile source 930, extracting bile from a source 940, and storing bile 950. The imaging system 600 may locate the bile source 300, for example, using a circle 610, and communicate its location, for example, using coordinate lines 611 and 612, to the targeting system 500. Targeting the bile source 920 may then be achieved using the targeting system 500. The targeting system 500 may target the bile source 300 with the extraction tool 400. The targeting system 500 may align the extraction tool 400 with the bile source 300 by moving the extraction tool 400 in multiple directions horizontally or vertically, and then the targeting system 500 may force the extraction tool 400 to puncture the bile source 300 and extract bile to be stored 950.

Turning now to exemplary FIG. 9, FIG. 9 displays an exemplary embodiment of a method of automated extraction. The method of automated extraction 900 may include locating a bile source 910, targeting a bile source 920, puncturing a bile source 930, extracting bile from a source 940, and storing bile 950. Once the bile source 300 has been located 910 and targeted 920, the bile source may be punctured 930 by the extraction tool 400. This may be achieved by one or more needles, or other extraction tools, moving towards the bile source 300. The bile may then be extracted 940 using the extraction tool 400. This may include suction or otherwise drawing the bile from the bile source 400. The bile may then be stored 950. The bile may be pumped into a remote storage tank. The bile may be stored in a storage tank. The storage tank may be a central storage tank connected to multiple extraction tools 400. The storage tank may hold and preserve bile. The extracted bile may then be frozen or preserved.

Figure 10:
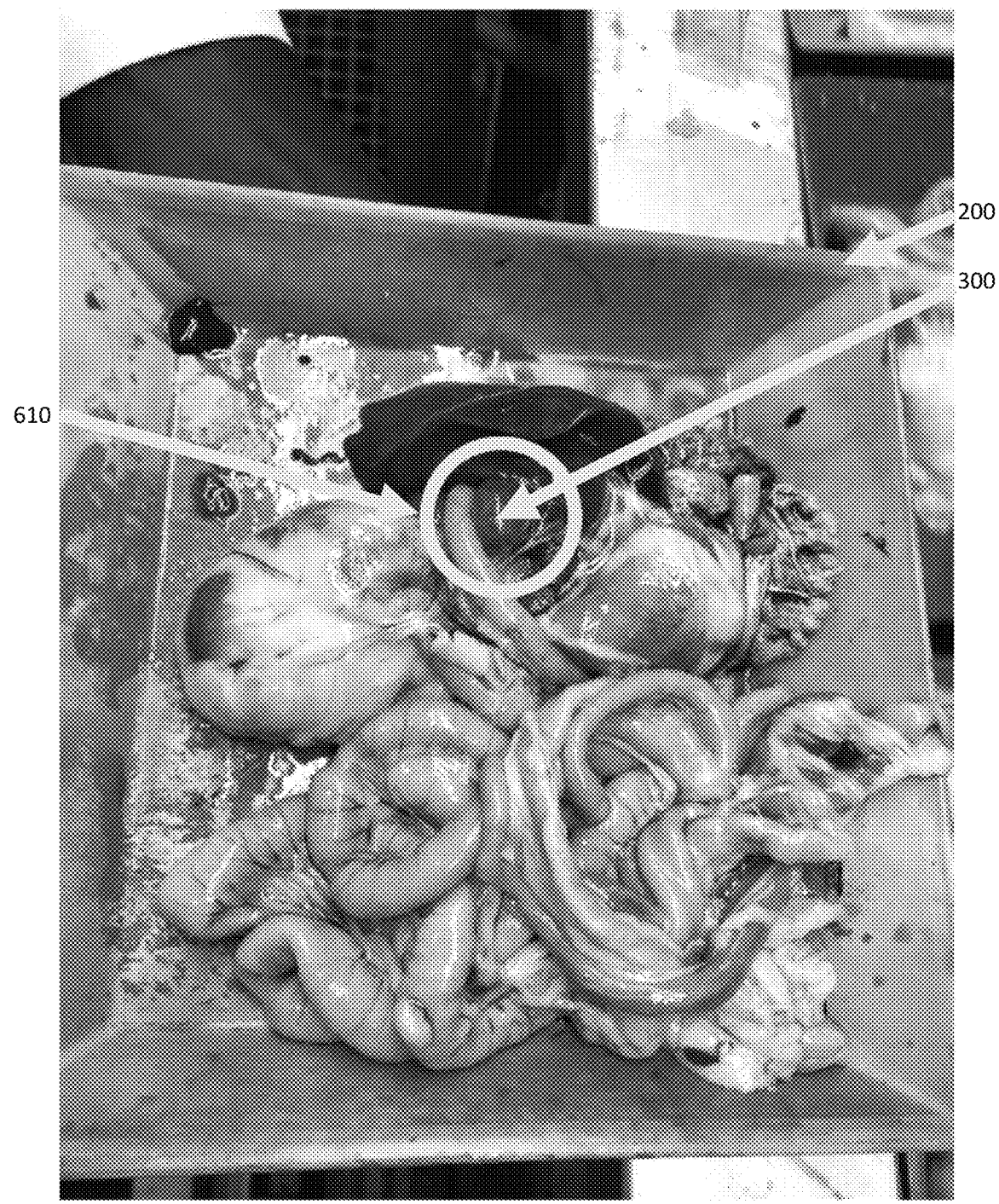
FIG. 10 is an exemplary embodiment of a bile source on a pan.

Turning now to exemplary FIG. 10, FIG. 10 displays a bile source on a pan. The bile source 300 may be a gall bladder surrounded by viscera. The bile source 300 may be on a pan 200. The circle 610, which may be used to target the bile source 300, is simulated.

Figure 11:
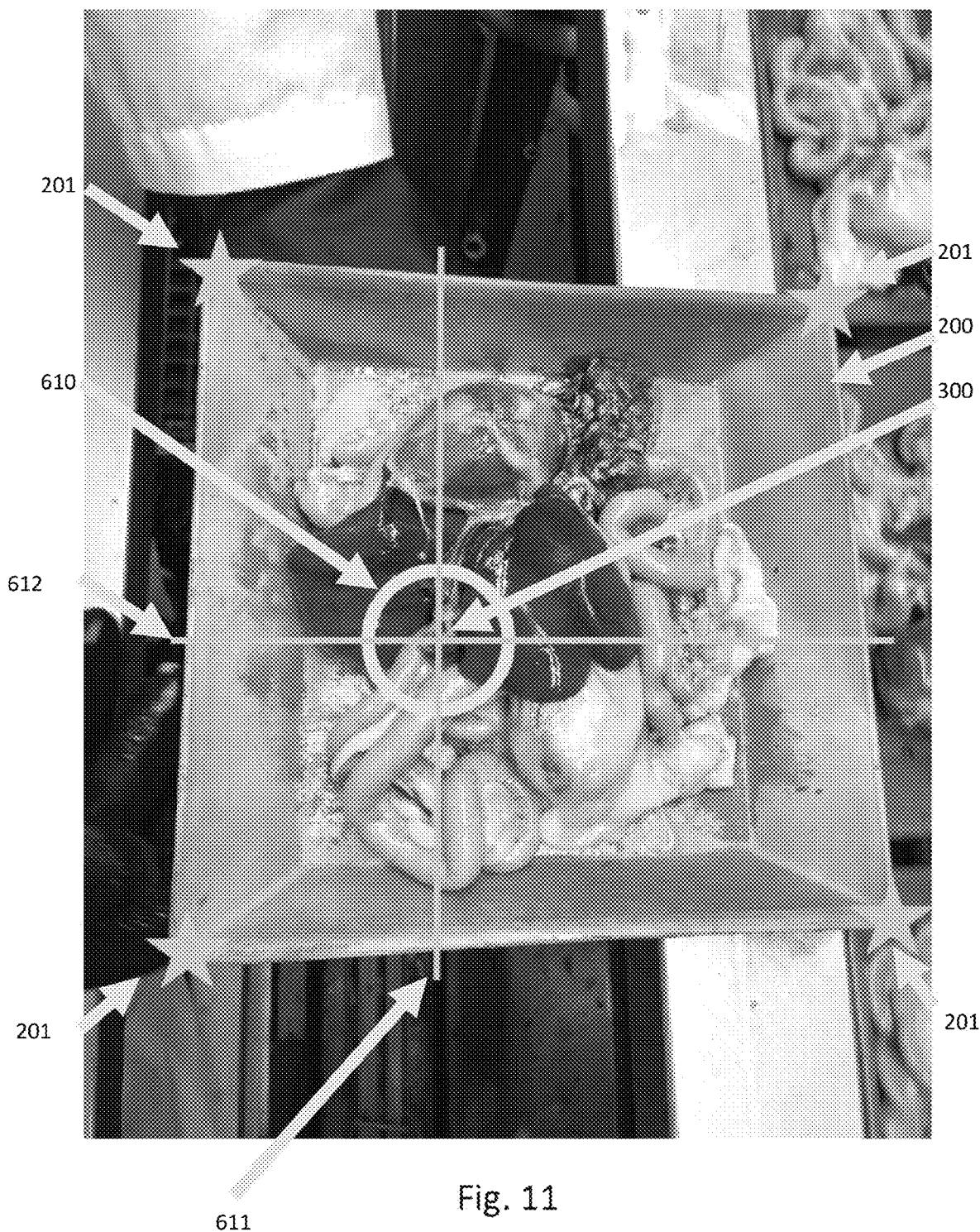
FIG. 11 is an exemplary embodiment of a bile source on a pan.

Turning now to exemplary FIG. 11, FIG. 11 displays a bile source on a pan. The bile source 300 may be a gall bladder surrounded by viscera. The bile source 300 may be on a pan 200. The bile source 300 may be located in relation to the corners 201 of the pan 200. The circle 610, and coordinates 611 and 612, which may be used to target the bile source 300, are simulated.

Figure 12:
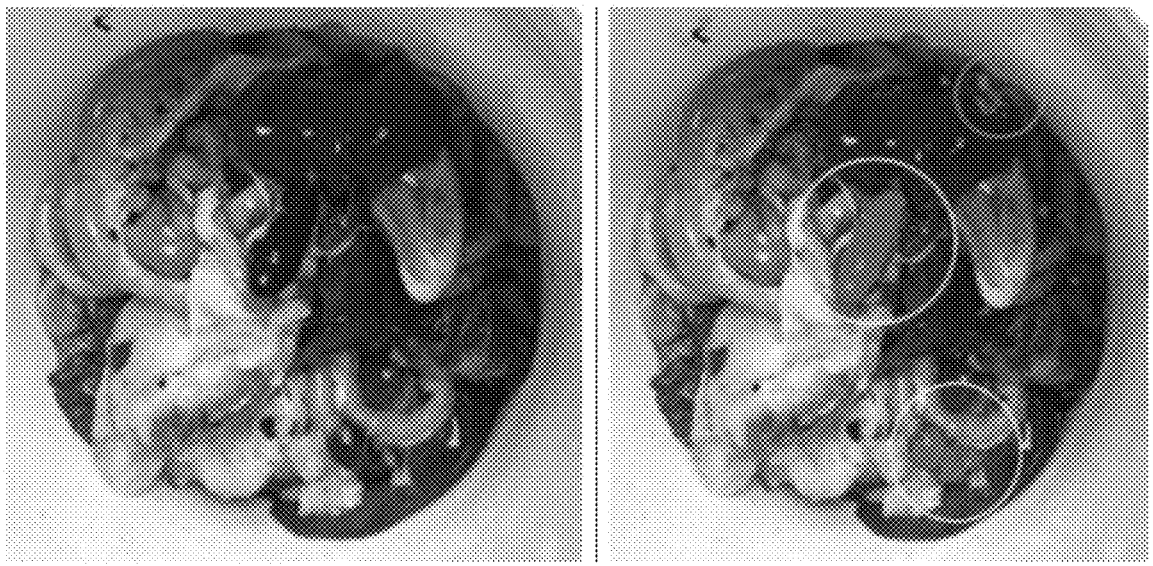
FIG. 12 is an exemplary embodiment of a bile source.

Turning now to exemplary FIG. 12, FIG. 12 displays a bile source.

Figure 13:
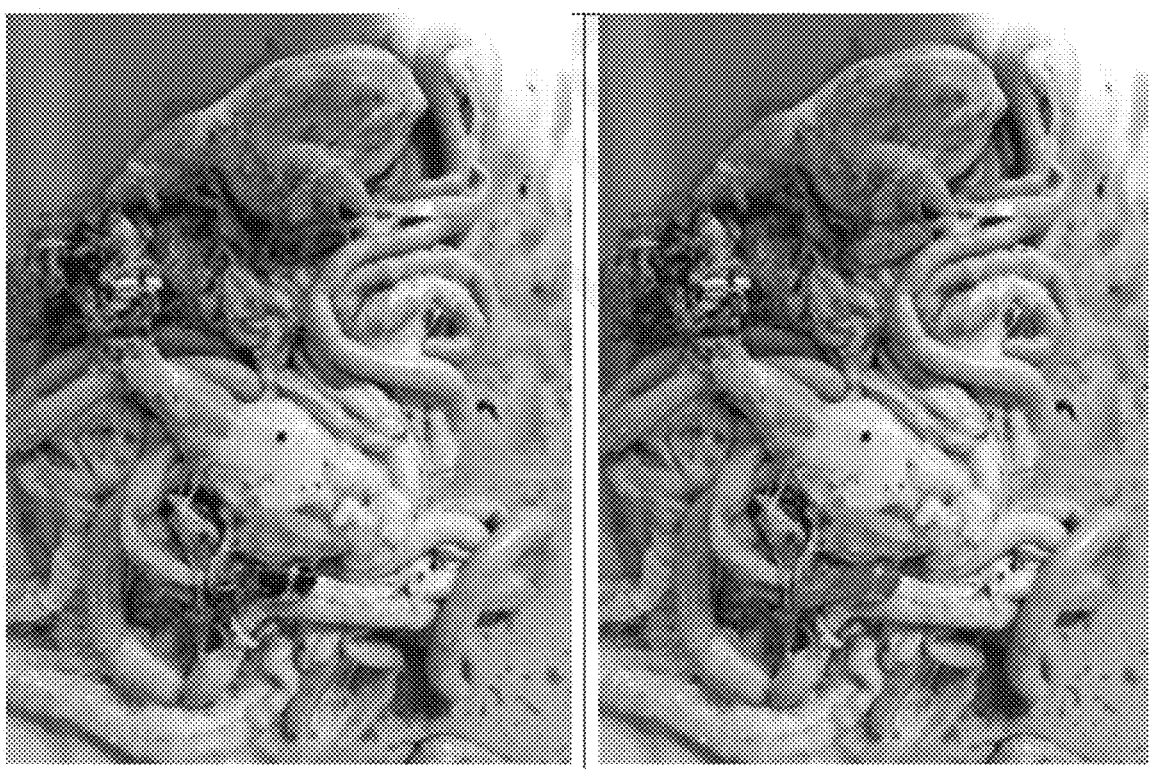
FIG. 13 is an exemplary embodiment of a bile source.

Turning now to exemplary FIG. 13, FIG. 13 displays a bile source.

Figure 14:
FIG. 14 is an exemplary embodiment of extracted bile.

Turning now to exemplary FIG. 14, FIG. 14 displays extracted bile.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A system of automated extraction of bile from a bile source comprising:
    a processing line;
    at least one pan for placement on the processing line, the at least one pan sized to receive a bile source;
    an imaging system configured to produce a field of view for capturing an image of a bile source in a pan on the processing line and to communicate a location of the bile source based on the image;
    a targeting system configured to receive the location communicated from the imaging system; and
    at least one extraction tool, the at least one extraction tool configured to puncture a bile source and extract bile by suction,
    wherein the targeting system is configured to move the at least one extraction tool to the location communicated from the imaging system.

2. The system according claim 1, wherein the processing line is equipped with a variable speed drive to operate continuously and by variable speed.

3. The system according to claim 1, wherein the imaging system is equipped with a timer to capture images according to a cycle time or a timing mechanism synchronized with movement of the processing line.

4. The system according to claim 1, wherein the extraction tool and the processing line share a single power shaft such that movement of the extraction tool is synchronized with movement of the processing line.

5. The system according to claim 1, wherein the targeting system is attached to the at least one extraction tool.

6. The system according to claim 1, further comprising a storage tank configured to receive the extracted bile from the at least one extraction tool.

7. A method of automated extraction of bile from a bile source, comprising:
- locating a bile source;
- targeting the located bile source;
- puncturing the bile source with at least one extraction tool; and
- extracting bile from the bile source by suction with an extraction tool.

8. The method according to claim 7, wherein targeting the located bile source comprises moving and aligning the at least one extraction tool with the bile source relative to the located bile source prior to puncturing.

9. The method according to claim 8, further comprising placing a bile source in a pan carried by a moveable processing line, wherein locating the bile source is relative to a position in the pan.

10. The method according to claim 9, further comprising styling the pan to facilitate locating the bile source in the pan.

11. The method according to claim 9, wherein at least one of locating the bile source and moving the extracting tool is synchronized with movement of the processing line.

12. The method according to claim 7, wherein locating the bile source comprises capturing an image of a bile source with an image system.

13. The method according to claim 7, further comprising storing the extracted bile.

14. An apparatus for automated extraction of bile from a bile source comprising:
- a processing line;
- at least one pan for placement on the processing line, the at least one pan sized to receive a bile source;
- an imaging system positioned proximate to the processing line, the imaging system being configured to produce a field of view for capturing an image of a bile source in a pan on the processing line and to communicate a location of the bile source based on the image;
- a targeting system positioned proximate to the processing line, the targeting system configured to receive the location communicated from the imaging system; and
- at least one extraction tool positioned proximate to the processing line, the at least one extraction tool being configured to puncture a bile source in a pan on the processing line and extract bile by suction,
- wherein the targeting system is configured to move the at least one extraction tool to the location communicated from the imaging system.

15. The apparatus according claim 14, wherein the processing line is equipped with a variable speed drive to operate continuously and by variable speed.

16. The apparatus according to claim 14, wherein the imaging system is equipped with a timer to capture images according to a cycle time or a timing mechanism synchronized with movement of the processing line.

17. The apparatus according to claim 14, wherein the extraction tool and the processing line share a single power shaft such that movement of the extraction tool is synchronized with movement of the processing line.

18. The apparatus according to claim 14, wherein the targeting system is attached to the at least one extraction tool.

19. The apparatus according to claim 14, further comprising a storage tank connected to at least one extraction tool.

20. A computer implemented method of synchronized moving, locating, targeting, and puncturing a bile source and extracting bile therefrom, the method comprising:
- moving a process line supporting a pan containing a bile source to an imaging system and a targeting system;
- receiving from the imaging system, a location of the bile source in the pan as process line moves the pan through the field of view, the location corresponding to a coordinate system defined by four corners of the pan; and
- communicating the location of the bile source in the pan as the process line moves the pan to the targeting system for aligning the at least one extraction tool with the location of the bile source in the pan, puncturing the bile source with the at least one aligned extraction tool, and suctioning bile from the bile source.

* * * * *